United States Patent [19]
Adams et al.

[11] Patent Number: 6,008,235
[45] Date of Patent: Dec. 28, 1999

[54] PYRIDYL SUBSTITUTED IMIDAZOLES

[75] Inventors: Jerry Leroy Adams, Wayne; Timothy Francis Gallagher, Harleysville; Ravi Shanker Garigipati, Wayne, all of Pa.

[73] Assignee: SmithKline Beecham Corporation, Philadelphia, Pa.

[21] Appl. No.: 08/995,086

[22] Filed: Dec. 19, 1997

Related U.S. Application Data

[62] Division of application No. 08/256,499, Nov. 22, 1994, Pat. No. 5,716,972, which is a continuation of application No. PCT/US93/00675, Jan. 13, 1993, which is a continuation-in-part of application No. 07/819,552, Jan. 13, 1993, abandoned.

[51] Int. Cl.$^6$ ..................... A61K 31/505; C07D 403/04
[52] U.S. Cl. ............................. 514/333; 544/333
[58] Field of Search ............................. 544/333; 514/256

[56] References Cited

U.S. PATENT DOCUMENTS 3,707,475  12/1972  Lombardino et al. ................ 546/278
3,961,062   6/1976  Lerch et al. ........................... 546/144

OTHER PUBLICATIONS

Dinarello et al., Rev.Infect.Disease, 6, p. 51 (1984).
Dinarello, J.Clin.Immun., 5(5), p. 287–297 (1985).
R.P.Soni, Aust.J.Chem., 35, p. 1493–6 (1982).
Poli et al., Proc.Nat'l Acad.Sci., 87, p. 782–784 (1990).
VanLeusen et al., J.O.C., 42, p. 1153 (1977).
Kumada et al., Tetrahedron Letters, 22, p. 5319 (1981).
Pridgen, J.Org.Chem., 47, p. 4319 (1982).
Stille, J.Amer.Chem.Soc., 109, p. 5478 (1978).
Fischer et al., Rec.Trav.Chim.Pays.Bas., 84, p. 439 (1965).
Snieckus, V., Tetrahedron Letters, 29, 2135 (1988).
Terashimia, M., Chem.Pharm.Bull., 11, p. 4755 (1985).
Thompson, W.J., et al., J.Org.Chem., 49, p. 5237 (1984).
Garigipati, R., Tetrahedron Letters, 31,p. 190 (1989).
Engel & Steglich, LiebigsAnn. Chem., 1916 (1978).
Strzybny et al., J.Org.Chem., 28, p. 3381 (1963).
Greene, T.W., Protecting Groups in Organic Synthesis, Wiley Intersci., New York, 1981.
Colotta et al., J. Immunol., 132(2), p. 936 (1985).
Simon et al., J. Immunol. Methods, 84, p. 85 (1985).
Becker et al., J. Immunol. 147, p. 4307 (1991).

*Primary Examiner*—Jane Fan
*Attorney, Agent, or Firm*—Dara L. Dinner; Stephen Venetianer; Chaarles M. Kinzig

[57] ABSTRACT

The novel compounds of Formula (I) have been found to be useful cytokine suppressive agents and therefore useful in the treatment and prophylaxis of disease states mediated thereby.

17 Claims, No Drawings

100 # PYRIDYL SUBSTITUTED IMIDAZOLES

This is a divisional of application Ser. No. 08/256,499 filed Nov. 22, 1994 (now allowed) now U.S. Pat. No. 5,716,972 which is the §371 entry of PCT/US93/00675, filed Jan. 13, 1993, WO 9,314,082 which is a continuation-in-part of U.S. Ser. No. 07/819,552, filed Jan. 13, 1992 (now abandoned).

FIELD OF THE INVENTION

This invention relates to novel compounds and methods of treating interleukin-1 (IL-1), interleukin-8 (IL-8), and Tumor Necrosis Factor (TNF) mediated diseases.

BACKGROUND OF THE INVENTION

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells.

Dinarello, J. Clinical Immunology, 5 (5), 287–297 (1985), reviews the biological activities which have been attributed to IL-1. It should be noted that some of these effects have been described by others as indirect effects of IL-1.

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T Cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Monokines, specifically TNF, are implicated in activated T-cell mediated HIV protein expression and/or virus replication by playing a role in maintaining T lymphocyte activation. Therefore, interference with monokine activity such as by inhibition of monokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T-cells, are targets for viral replication and the level of viral replication is dependent upon the activation state of the cells. [See Rosenberg et al., The Immunopathogenesis of HIV Infection, Advances in Immunology, Vol. 57, (1989)]. Monokines, such as TNF, have been shown to activate HIV replication in monocytes and/or macrophages [See Poli, et al., Proc. Natl. Acad. Sci., 87:782–784 (1990)], therefore, inhibition of monokine production or activity aids in limiting HIV progression as stated above for T-cells.

TNF has also been implicated in various roles with other viral infections, such as the cytomegalia virus (CMV), influenza virus, and the herpes virus for similar reasons as those noted.

Interleukin -8 (IL-8) is a chemotactic factor first identified and characterized in 1987. IL-8 is produced by several cell types including mononuclear cells, fibroblasts, endothelial cells, and ketainocytes. Its production from endothelidl cells is induced by IL-1, TNF, or lipopolysachharide (LPS). Human IL-8 has been shown to act on Mouse, Guinea Pig, Rat, and Rabbit Neutrophils. Many different names have been applied to IL-8, such as neutophil attractant/activation protein-1 (NAP-1), monocyte derived neutrophil chemotactic factor (MDNCF), neutrophil activating factor (NAF), and T-cell lymphocyte chemotactic factor.

IL-8 stimulates a number of functions in vitro. It has been shown to have chemoattractant properties for neutophils, T-lymphocutes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutophils into the inflammatory site) would benefit by compounds which are suppresive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

There remains a need for treatment, in this field, for compounds which are cytokine suppresive antiinflammatory drugs (hereinafter CSAID's), i.e. compounds which are capable of inhibiting cytokines, such as IL-1, IL-6, IL-8 and TNF.

SUMMARY OF THE INVENTION

This invention relates to the novel compounds of Formula (I) and pharmaceutical compositions comprising a compound of Formula (I) and a pharmaceutically acceptable diluent or carrier.

This invention also relates to a method of treating a cytokine mediated disease, in a mammal in need thereof which comprises administering to said mammal an effective amount of a compound of Formula (I).

This invention more specifically relates to a method of inhibiting the production of IL-1 in a mammal in need thereof which comprises administering to said mammal an effective amount of a compound of Formula (I).

This invention more specifically relates to a method of inhibiting the production of IL-8 in a mammal in need thereof which comprises administering to said mammal an effective amount of a compound of Formula (I).

This invention more specifically relates to a method of inhibiting the production of TNF in a mammal in need thereof which comprises administering to said mammal an effective amount of a compound of Formula (I).

This invention more specifically relates to a method of treating a human, afflicted with a human immunodeficiency virus (HIV), which comprises administering to said human an effective TNF inhibiting amount of a compound of Formula (I).

The novel compounds of this invention are represented by the structure:

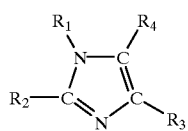

(I)

wherein $R_1$ is a mono- or di-substituted 4-quinolyl, 4-pyridyl, 1-imidazolyl, 1-benzimidazolyl, 4-pyrimidinyl wherein the substituent is independently selected from the group consisting of hydrogen, $C_{1-4}$ alkyl, halo, $O-C_{1-4}$ alkyl, $S-C_{1-4}$ alkyl, or $N(R_a)_2$;

$R_a$ is hydrogen, $C_{1-6}$ alkyl, or $R_a$ together with the nitrogen, may form a heterocyclic ring of 5 to 7 members, said ring optionally containing an additional heteroatom selected from the group consisting of oxygen, sulfur or nitrogen;

$R_2$ is mono- or di-substituted phenyl wherein the substituents are independently selected from the group consisting of hydrogen, halo, $S(O)_m R_5$, $OR_6$, halo substituted $C_{1-4}$ alkyl, $C_{1-4}$ alkyl, or $N(R_{12})_2$;

$R_4$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, heterocyclic, heterocyclicalkyl, aryl, aryl alkyl, heteroaryl, heteroaryl alkyl;

$R_3$ is $(X)_r-(Q)_s-(Y)_t$;

X is hydrogen, $-(C(R_{10})_2)_n-$, $-NR_{13}-$, $-O-$, or $S(O)_m$;

r is a number having a value of 0 or 1;

m is a number having a value of 0, 1 or 2;

Q is alkenyl, alkynyl, cycloalkyl, cycloalkenyl, heterocyclic, heterocyclicalkyl, aryl, arylalkyl, heteroaryl, or heteroarylalkyl;

s is a number having a value of 0 or 1;

Y is a substituent selected from the group consisting of hydrogen, $C_{1-10}$ alkyl, halo-substituted $C_{1-10}$ alkyl, halogen, $-(C(R_{10})_2)_n OR_8$, $-(C(R_{10})_2)_n NO_2$, $-(C(R_{10})_2)_n S(O)_{m'} R_{11}$, $-(C(R_{10})_2)_n SR_8$, $-(C(R_{10})_2)_n S(O)_m OR_8$, $-(C(R_{10})_2)_n S(O)_m NR_8 R_9$, $-X_a-P(Z)-(X_a R_{13})_2$, $-(C(R_{10})_2)_n NR_8 R_9$, $-(C(R_{10})_2)_n CO_2 R_8$, $-(C(R_{10})_2)_n OC(O)-R_8$, $-(C(R_{10})_2)_n CN$, $-(C(R_{10})_2)_n CONR_8 R_9$, $-(C(R_{10})_2)_n C(S)NR_8 R_9$, $-(C(R_{10})_2)_n NR_{10} C(O) R_8$, $-(C(R_{10})_2)_n NR_{10} C(S) R_8$, $-(C(R_{10})_2)_n NR_{10} C(Z) NR_8 R_9$, $-(C(R_{10})_2)_n NR_{10} S(O)_m R_{11}$, $-(C(R_{10})_2)_n NR_{10} C(=NCN)-S-R_{11}$, $-(C(R_{10})_2)_n NR_{10} C(=NCN)-NR_8 R_9$, $-(C(R_{10})_2)_n NR_{10} C(O) C(O)-NR_8 R_9$, $-(C(R_{10})_2)_n NR_{10} C(O) C(O)-OR_{10}$, $-(C(R_{10})_2)_n C(=NR_{10})-NR_8 R_9$, $-(C(R_{10})_2)_n-C(=NR_{10})-ZR_{11}$, $-(C(R_{10})_2)_n-OC(Z)-NR_8 R_9$, $-(C(R_{10})_2)_n NR_{10} S(O)_m CF_3$, $-(C(R_{10})_2)_n NR_{10} C(O) OR_{10}$;

t is an integer having a value of 0, 1, 2, or 3;

Xa is independently $-(C(R_{10})_2)_n-$, $-NR_8-$, $-O-$ or $-S-$;

Z is oxygen or sulfur, m' is an integer having a value of 1 or 2;

n is an integer having a value of 0 to 10;

$R_5$ is hydrogen, $C_{1-4}$ alkyl, $C_{2-4}$ alkenyl, $C_{2-4}$ alkynyl, $C_{3-7}$ cycloalkyl, $C_{5-7}$ cycloalkenyl, aryl, or $N(R_7)_2$; provided that when m is 1 or 2 then $R_5$ is not hydrogen.

$R_6$ is hydrogen, $C_{1-4}$ alkyl, halo substituted $C_{1-4}$ alkyl, $C_{2-4}$ alkenyl, $C_{2-4}$ alkynyl, $C_{3-7}$ cycloalkyl, $C_{5-7}$ cycloalkenyl, or aryl;

$R_7$ is hydrogen, $C_{1-4}$ alkyl, $C_{2-4}$ alkenyl, $C_{2-4}$ alkynyl, aryl, or may form a heterocyclic ring of 5 to 7 members together with the nitrogen, said ring optionally containing an additional heteroatom selected from the group consisting of oxygen, sulfur or nitrogen; provided that when $R_5$ is $N(R_7)_2$ then m is 1 or 2;

$R_8$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, heterocyclic, heterocyclic alkyl, aryl, aryl alkyl, heteroaryl, heteroaryl alkyl;

$R_9$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl alkyl, heteroaryl, heteroaryl alkyl or $R_8$ and $R_9$ may together form a heterocyclic ring of 5 to 7 members together with the nitrogen, said ring optionally containing an additional heteroatom selected from the group consisting of oxygen, sulfur or nitrogen;

$R_{10}$ is hydrogen, or $C_{1-4}$ alkyl;

$R_{11}$ is $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl alkyl, heteroaryl, heteroaryl alkyl;

$R_{12}$ is hydrogen, $C_{1-4}$ alkyl, aryl, or may form a heterocyclic ring of 5 to 7 members together with the nitrogen;

$R_{13}$ is hydrogen, $C_{1-10}$ alkyl, cycloalkyl, heterocyclic, aryl, aryl alkyl, heteroaryl, or heteroaryl alkyl;

or a pharmaceutically acceptable salt thereof.

DETAILED DESCRIPTION OF THE INVENTION

This invention relates to a method of inhibiting the production of cytokines in a mammal in need thereof which comprises administering to said mammal an effective amount of a compound of Formula (I).

The compounds of Formula (I) are useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibitors of Formula (I). Such viruses include, but are not limited to; HIV-1, HIV-2 and HIV-3, Cytomegalovirus (CMV), Influenza, adenovirus and the Herpes group of viruses, such as but not limited to, Herpes Zoster and Herpes Simplex.

This invention more specifically relates to a method of treating a human, afflicted with a human immunodeficiency virus (HIV), which comprises administering to such mammal an effective TNF inhibiting amount of a compound of Formula (I).

The compounds of Formula (I) may also be used in association with the veterinary treatment of animals, other than in humans, in need of inhibition of TNF production. TNF mediated diseases for treatment, therapeutically or prophylactically, in animals include disease states such as those noted above, but in particular viral infections. Examples of such viruses include, but are not limited to, the lentivirus infections such as equine infectious anaemia virus, caprine arthritis virus, visna virus, or the maedi virus, or the retroviruses, such as feline immunodeficiency virus (FIV), bovine immunodeficiency virus, or canine immunodeficiency virus.

For purposes herein of nomenclature the compounds of Formula (I) are named by their position corresponding to:

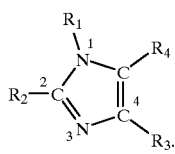

Preferred compounds of Formula (I) are those wherein $R_4$ is hydrogen or $C_{1-10}$ alkyl. More preferred is where $R_4$ is hydrogen or methyl.

Preferred $R_1$ moieties are 4-pyridyl and 4-quinolyl. More preferred is 4-pyridyl. A preferred substituent for all $R_1$ moieties is $C_{1-4}$ alkyl, more preferably methyl. Most preferred for $R_1$ is a 2-alkyl-4-pyridyl, such as 2-methyl-4-pyridyl.

Preferred $R_2$ substituent groups on the phenyl ring are hydrogen or halogen. Preferred halogens are fluoro and chloro. Preferred ring substitution is in the 3- and 4-positions.

Preferred $R_3$ moieties are hydrogen, alkyl, aryl, and heteroaryl either attached directly to the imdiazole ring, such as methyl, phenyl, pyridine, or pyrimidine, or by attachment thru a heteroatom, such as oxygen or sulfur, including but not limited to alkoxy, thioalkyl, benzyloxy, phenoxy, all optionally substituted by Y terms. Additionally preferred moieties for $R_3$ are alkyl or phenyl substituted independently one or more time by halogen, $—(C(R_{10})_2)_nOR_8$, $—(C(R_{10})_2)_nS(O)_{m'}R_{11}$, $—(C(R_{10})_2)_nSR_8$, $—(C(R_{10})_2)_nS(O)_{m'}OR_8$, $—(C(R_{10})_2)_nS(O)_{m'}NR_8R_9$, $—X_a—P(Z)—(X_aR_{13})_2$, $—(C(R_{10})_2)_nNR_8R_9$, $—(C(R_{10})_2)_nCO_2R_8$, $—(C(R_{10})_2)_nOC(O)—R_8$, $—(C(R_{10})_2)_nCONR_8R_9$, $—(C(R_{10})_2)_nNR_{10}C(=NCN)—NR_8R_9$, or $—(C(R_{10})_2)_nNR_{10}S(O)_mR_{11}$.

More preferably the $R_3$ substitution is $—(C(R_{10})_2)_nOR_8$, $—(C(R_{10})_2)_nS(O)_{m'}R_{11}$, $—(C(R_{10})_2)_nNR_8R_9$, $—(C(R_{10})_2)_nCO_2R_8$, $—(C(R_{10})_2)_nS(O)_{m'}NR_8R_9$, or $—(C(R_{10})_2)_nNR_{10}S(O)_mR_{11}$. Most preferably the substituents are hydroxyl, methylthio, carboxylic acid, methylamino, N,N-dimethylaminomethyl, and the sulfonamide derivatives.

When $R_3$ is $—X_a—P(Z)—(X_aR_{13})_2$, the $X_a$ moiety in $—X_a—P(Z)—(X_aR_{13})_2$ is preferably oxygen, or the moiety $—(C(R_{10})_2)_n$ wherein n is 0 to 2, Z and the remaining Xa terms are oxygen.

A preferred subgenus of compounds for formula (I) is where 4-pyridyl, 2-alkyl-4-pyridyl, or 4-quinolyl; $R_4$ is hydrogen or methyl, $R_{10}$ is hydrogen or methyl, $R_8$ is hydrogen or alkyl, or where appropriate $R_8$ and $R_9$ cyclize to form a 5 membered saturated heterocyclic ring, $R_2$ is phenyl, or phenyl mono- or di-substituted with fluoro or chloro; $R_3$ is alkyl, phenyl or phenyl alkyl substituted with $—(C(R_{10})_2)_nOR_8$, $—(C(R_{10})_2)_nS(O)_mR_{11}$, $—(C(R_{10})_2)_nSR_8$, $—(C(R_{10})_2)_nS(O)_mOR_8$, $—(C(R_{10})_2)_nS(O)_mNR_8R_9$, $—X_a—P(Z)—(X_aR_{13})_2$, $—(C(R_{10})_2)_nNR_8R_9$, $—(C(R_{10})_2)_nCO_2R_8$, $—(C(R_{10})_2)_nOC(O)—R_8$, $—(C(R_{10})_2)_nCONR_8R_9$, $—(C(R_{10})_2)_nNR_{10}C(=NCN)—NR_8R_9$, or $—(C(R_{10})_2)_nNR_{10}S(O)_mR_{11}$.

In all instances herein where there is an alkenyl or alkynyl moiety as a substituent group, such as in $R_5$, $R_7$, $R_8$, $R_9$, or $R_{11}$ the unsaturated linkage, i.e., the vinylene or acetylene linkage is preferably not directly attached to the nitrogen, oxygen or sulfur moieties, for instance in Y as $—(C(R_{10})_2)_nNR_{10}C(Z)NR_8R_9$, $C(=NR_{10})—ZR_{11}$ or $OR_8$.

By the term "halo" as used herein is meant all halogens, i.e., chloro, fluoro, bromo and iodo.

By the term "$C_{1-10}$alkyl" or "alkyl" groups as used herein is meant to include both straight or branched chain radicals of 1 to 10 carbon atoms, unless the chain length is limited thereto, including, but not limited to methyl, ethyl, n-propyl, isopropyl, n-butyl, sec-butyl, isobutyl, tert-butyl, and the like.

By the term "heterocyclic" as used herein, in any combination, such as "heterocyclic alkyl" is meant a 5–10 membered ring system in which one or more rings contain one or more heteroatoms selected from the group consisting of N, O, or S; such as but not limited to pyrrolidine, piperidine, piperazine, morpholine, imidazolidine, or pyrazolidine.

By the term "aryl" as used herein is meant phenyl, or naphthyl.

By the term "heteroaryl" as used herein, in any combination, such as "heteroaryloxy", is meant a 5–10 membered aromatic ring system in which one or more rings contain one or more heteroatoms selected from the group consisting of N, O or S; such as, but not limited to, quinoline, isoquinoline, pyridine, pyrimidine, oxazole, thiazole, thiadiazole, triazole, imidazole.

By the term "sulfinyl" as used herein is meant the oxide of the corresponding sulfide. By the term "thio" as used herein is meant the sulfide.

By the term "mammal" as used herein includes humans.

By the term "inhibiting the production of the cytokine (IL-1, IL-8 or TNF)" is meant a) a decrease of excessive in vivo levels of the cytokine (IL-1, IL-8 or TNF) in a human to normal levels or below normal levels by inhibition of the in vivo release of the cytokine (IL-1, IL-8 or TNF) by all cells, including but not limited to monocytes or macrophages;

b) a down regulation, at the genomic level, of excessive in vivo levels of the cytokine (IL-1, IL-8 or TNF) in a human to normal levels or below normal levels; or c) a down regulation, by inhibition of the direct synthesis of the cytokine (IL-1, IL-8 or TNF) as a postranslational event.

d) a down regulation, at the translational level, of excessive in vivo levels of the cytokine (IL-1, IL-8 or TNF) in a human to normal or sub-normal levels.

By the term "TNF mediated disease or disease state" is meant any and all disease states in which TNF plays a role, either by production of TNF itself, or by TNF causing another monokine to be released, such as but not limited to IL-1, or IL-6. A disease state in which IL-1, for instance is a major component, and whose production or action, is exacerbated or secreted in response to TNF, would therefore be considered a disease stated mediated by TNF.

By the term "cytokine" as used herein is meant any secreted polypeptide that affects the functions of cells and is a molecule which modulates interactions between cells in the immune, inflammatory or hematopoietic response. A cytokine includes, but is not limited to, monokines and lymphokines regardless of which cells produce them. For instance, a monokine is generally referred to as being produced and secreted by a mononuclear cell, such as a macrophage and/or monocyte but many other cells produce monokines, such as natural killer cells, fibroblasts, basophils, neutraphils, endothelial cells, brain astrocytes, bone marrow stromal cells, epideral keratinocytes, and β-lymphocytes. Lymphokines are generally referred to as being produced by lymphocyte cells. Examples of cytokines include, but are not limited to, Interleukin-1 (IL-1), Interleukin-6 (IL-6), Tumor Necrosis Factor-alpha (TNF-α) and Tumor Necrosis Factor beta (TNF-β).

By the term "cytokine interfering or cytokine suppresive amount" is meant an effective amount of a compound of Formula (I) which will, cause a decrease in the in ivo levels of the cytokine to normal or sub-normal levels, when given to the patient for the prophylaxis or therapeutic treatment of a disease state which is exacerbated by, or caused by, excessive or unregulated cytokine production.

As used herein, the cytokine referred to in the phrase "inhibition of a cytokine, for use in the treatment of an HIV infected human" is a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

The compounds of the present invention may contain one or more asymmetric carbon atoms and may exist in racemic and optically active forms. All of these compounds are contemplated to be within the scope of the present invention. Exemplified compounds of Formula (I) are:

1-(4-pyridyl)-2-(4-fluorophenyl)-4-phenylimidazole;
1-(4-pyridyl)-2-(4-fluorophenyl)-4-(4-hydroxyphenyl) imidazole;
1-(4-pyridyl)-2-(4-fluorophenyl)-4-(4-thiomethylphenyl) imidazole;
1-(4-pyridyl)-2-(4-fluorophenyl)-4-(4-methylsulfinylphenyl)imidazole;
1-(4-pyridyl)-2-(4-fluorophenyl)-4-(4-methylsulfonylphenyl)imidazole;
1-(4-pyridyl)-2-(4-fluorophenyl)-4-methylimidazole;
1-(4-pyridyl)-2-(4-N,N-dimethylaminomethylphenyl) imidazole;
1-(4-pyridyl)-2-(4-fluorophenyl)-4-(benzyloxy)imidazole;
1-(2-methyl-4-pyridyl)-4-(4-methylsulfinylphenyl) imidazole;
1-(2-methyl-4-pyridyl)-4-(4-thiomethylphenyl)imidazole; or
1-(2-methyl-4-pyridyl)-4-(3-chlorophenyl)imidazole.

METHODS OF PREPARATION

Preparation of the compounds of Formula (I) can be carried out by one of skill in the art according to the procedures outlined in the Examples, infra. The preparation of any remaining compounds of Formula (I) not described therein may be prepared by the analogous processes disclosed herein.

Scheme I

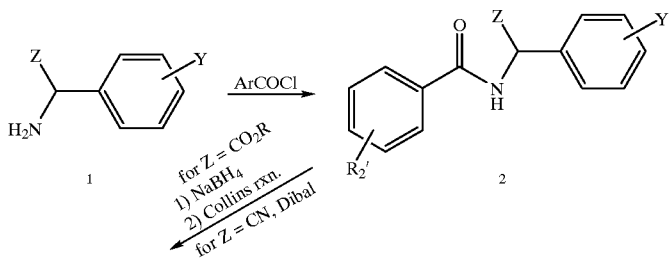

-continued

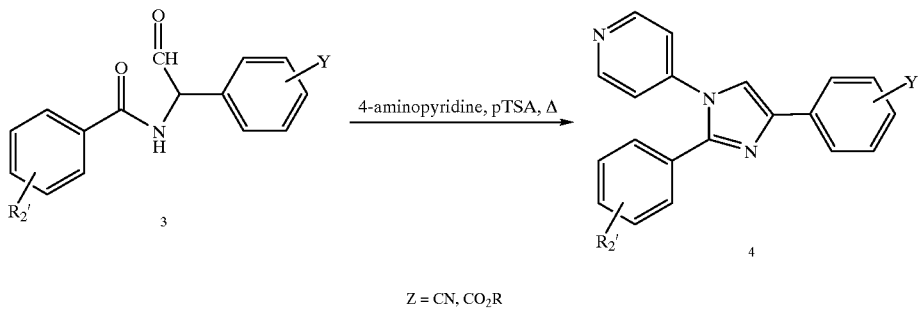

Z = CN, CO₂R

Compounds of this invention (wherein r is 0, and s is 1) may be prepared starting from the α-amino esters or nitrites 1 (illustrated in Scheme 1 for an aryl compound, but the method is also applicable to alkyl α-amino esters or nitrites). Compounds 1 are readily available from the corresponding aldehyde using the Strecker procedure or other standard methods. Acylation of 1 with an acid chloride affords the amides 2, which are converted to the aldehyde amides 3, either directly by reduction with the appropriate hydride-based reagent, for example when Z=CN or CO₂R by reduction with diisobutylaluminum hydride (DIBAL), or for Z=CO₂R by first reduction of the ester to the alcohol, followed by subsequent oxidation back to the aldehyde oxidation state of compound 3. Alternatively, in some cases it may be more convenient to begin with compound 1 as the protected alcohol or aldehyde [Z=CH₂OR or CH(OR)₂] and subsequently deprotect and oxidize if needed to prepare 3 following the initial acylation step (1 to 2). Reaction of 3 with the required amino heterocycle (R₁ term) using acidic catalysis affords compound 4. The R₂' moiety represents the generic substitution terms as used for the R2 moiety in formula (I). The R₂' and Y substituent groups are suitably unreactive moieties under the conditions noted above. Reactive substituent groups, such as the S(O)ₘ moiety of R₂' under conditions when Z is CO₂R and the Collins reaction is used, etc., are readily obvious to one skilled in the art.

Scheme II

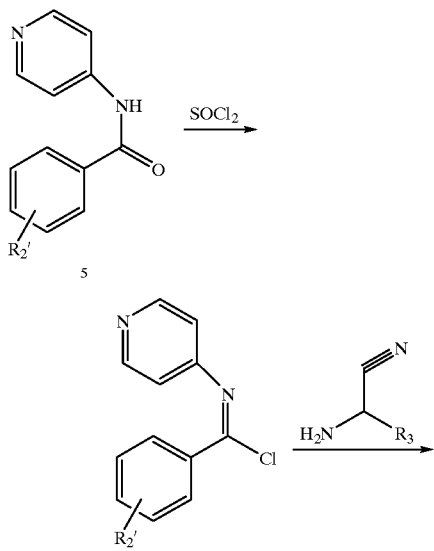

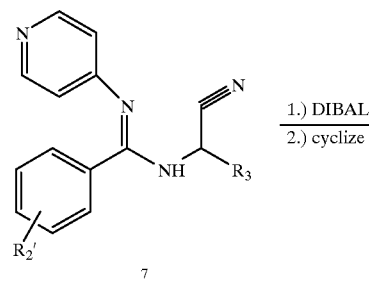

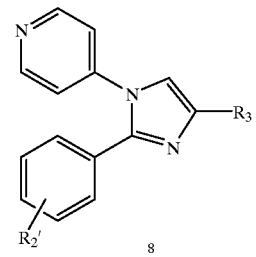

An additional method of imidazole synthesis utilizes the amides 5 prepared from readily available starting materials using standard coupling chemistry, such as that employed for the synthesis of pedtides (Scheme II). In addition more vigorous methods such as the reaction of the ester or acid of the acyl partner and the appropriate heterocyclic amine (for the example in Scheme II, 4-aminopyridine) at elevated temperatures 100–300° C. with or without a solvent may be used to prepare 5. Conversion of 5 to the imidoyl halide 6 followed by reaction with an α-amino nitrile (available as the initial product of the Strecker synthesis used in Scheme I) produces the amidine of structure 7. Reduction of the nitrile with a metal hydride reducing agent, preferably diisobutylaluminum hydride (DIBAL), affords the intermediate imine which can be cyclized, preferably with acid in a subsequent step to afford 8.

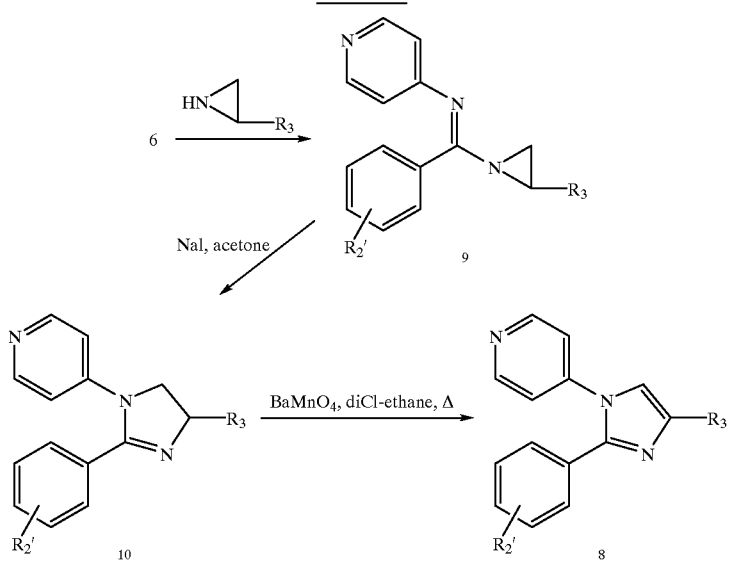

Scheme III

Condensation of the imidoyl halide 6 (illustrated in scheme II) may also be performed with an aziridine to form the amidine derivative 9 (Scheme III). Reaction of 9 with an alkili halide in an appropriate solvent, preferably NaI in acetone yields the intermediate dihydroimidazole 10 which can be dehydrogenated by heating 10 in an inert solvent with a variety of metal catalysis or by oxidation, preferably using $BaMnO_4$ to produce the imidazole 8.

If a 2-carboalkoxy aziridine is used, for example 2-carboethoxy aziridine, the resulting imidazole with $R_3$=$CO_2Et$ can be prepared. Basic hydrolysis (NaOH) of the ester affords the carboxylic acid which may be converted to the acid chloride by treatment with oxalyl chloride. Treatment of the acid chloride with an amine affords an amide, or with a metal azide affords the acyl azide. Thermal Beckman rearrangement of the acyl azide yields the isocyanate $R_3$=—NCO, which can be reacted with either oxygen, nitrogen or sulfur nucleophiles to produce the corresponding carbamate, urea, or thiocarbamate, respectively. Alternatively, the Hunsdieker reaction (treatment of the silver salt of the carboxylic acid with bromine) or variations thereof may be used to convert the acid to the rearranged bromide, $R_3$=Br. Transmetalation of the bromide to the ogranolithium, using either n- or t-butyl lithium in an ethereal solvent, followed by addition of a dialkyl phosphorochloridate, such as dimethyl chlorophosphate, may be used to prepare the phosphonate ester, $R_3$=$P(=O)(OR)_2$.

In Schemes I, II, and III the $R_3$ and Y terms may be an appropriately protected alcohol for example in Scheme III a silyl ether, such as t-butyldimethyl or t-butyldiphenyl, and in Schemes I and II an alkyl ether, such as methyl connected by an alkyl chain of variable link, $(C(R_{10})_2)_nR_3$/Y. Following cyclization to the imidazole the alcohol is deprotected using standard reaction conditions to afford the free alcohol. The alcohol may be oxidized to the carboxylic acid (chromic acid or pryidimium dichromate in dimethyl form amide) and subsequently converted to the ester (acid catalysis in the presence of an alcohol or carbonyl diimidazole followed addition of a basic solution of the alcohol). The alcohol may also be oxidized to the aldehyde (Swern's reagent or pyridinium chlorochromate in methylene chloride) and condensed with $NH_3$, or a primary or secondary amine in the presence of $NaCNBH_3$, the Borch reductive amination procedure, to prepare the corresponding primary, secondary and tertiary amines, respectively. Alternatively the alcohol may be activated for displacement by either nitrogen, sulfur or phosphorus nucleophiles. For example, reaction of the alcohol with diisopropyl azodicarboxylate, triphenyl phosphine, and thioacetic acid produces the corresponding thioester which can be hydrolized to the thiol and oxidized to the sulfonic acid Additional derivatives which may be prepared from the above compounds are: $C(O)NR_8R_9$ from the —$CO_2CH_3$ by heating with or without catalytic metal cyanide, e.g. NaCN, and $HNNR_8R_9$ in $CH_3OH$; —$OC(O)R_8$ from the —OH with e.g., $ClC(O)R_8$ in pyridine; —$NR_{10}$—$C(S)NR_8R_9$ from —$NHR_{10}$ with an alkylisothiocyante or thiocyanic acid; $NR_6C(O)OR_6$ from —$NHR_6$ with the alkyl chloroformate; —$NR_{10}C(O)NR_8R_9$ from the —$NHR_{10}$ by treatment with an isocyanate, e.g. $HN=C=O$ or $R_{10}N=C=O$; —$NR_{10}$—$C(O)R_8$ from the —$NHR_{10}$ by treatment with Cl—$C(O)R_8$ in pyridine; —$C(=NR_{10})NR_8R_9$ from —$C(NR_8R_9)SR_8$ with $H_3NR8^+OAc^-$ by heating in alcohol; —$C(NR_8R_9)SR_8$ from —$C(S)NR_8R_9$ with $R_6$-I in an inert solvent, e.g. acetone; —$C(S)NR_8R_9$ where $R_8$ or $R_9$ is not hydrogen from $C(S)NH_2$ with $HNR_8R_9$, $C(=NCN)$—$NR_8R_9$ from —$C(=NR_8R_9)$—$SR_8$ with $NH_2CN$ by heating in anhydrous alcohol, alternatively from $C(=NH)$—$NR_8R_9$ by treatment with Br—CN and NaEtO— in EtOH; $NR_{10}$—$C(=NCN)SR_8$ from $NHR_{10}$ by treatment with $(R_8S)_2C=NCN$; —$NR_{10}SO_2R_8$ from $NHR_{10}$ by treatment with $ClSO_2R_8$ by heating in pyridine; —$NR_{10}C(S)R_8$ from —$NR_{10}C(O)R_8$ by treatment with Lawesson's reagent [2,4-bis(4-methoxyphenyl)-1,3,2,4-dithiadiphosphetane-2,4-disulfide]; —$NR_{10}SO_2CF_3$ from $NHR_6$ with triflic anhydride and base; $NR_{10}C(O)$—$C(O)$—$OR_8$ from —$NHR_{10}$ with, e.g. methyloxalyl chloride and a base such as triethylamine; —$NR_{10}C(O)$—$C(O)$—$NR_8R_9$ from —$NR_{10}C(O)$—$C(O)$—$OR_8$ with $HNR_8R_{79}$; 1-($NR_{10}$)-2-imidazolyl from —$C(=NH)NHR_{10}$ by heating with 2-chloroacetaldehyde in chloroform.

SYNTHETIC EXAMPLES

The following examples are illustrative and are not limiting of the compounds of this invention.

Example 1

1-(4-Pyridyl)-2-(4-fluorophenyl)-4-phenylimidazole
Ethyl phenylglycine, hydrochloride To a mixture of phenylglycine (15.00 gram (hereinafter g.), 0.1 mole (hereinafter mol)) in EtOH (100 miliLiters (hereinafter mL)) was added 20% ethanolic HCl (30 mL). The mixture was heated at reflux for about 20 hours (hereinafter h.), then allowed to cool. The solvent was removed in vacuo, and the residue was used without further purification.
N-(4-Fluorobenzoyl)phenylglycine, ethyl ester To a solution of ethyl phenylglycine, hydrochloride (prepared above) in $CH_3CN$ (60 mL) were added 4-fluorobenzoyl chloride (25.4 g, 0.16 mol) and pyridine. The resulting mixture was stirred at room temperature for about 5.5 h, then was partitioned between aqueous $NaHCO_3$ and EtOAc. The organic extract was washed successively with 10% aqueous NaOH, 3 N HCl and saturated aqueous NaCl. The solvent was removed in vacuo, and the residue was crystallized from $CH_2Cl_2$/hexanes to afford the title compound (19 g, 63%).
4-Fluoro-N-(2-hydroxy-1-phenyl)ethylbenzamide To a solution of N-(4-fluoro-benzoyl)phenylglycine, ethyl ester (1.56 g, 5.2 mmol) in THF (15 mL) was added sodium borohydride (0.50 g, 12.9 mmol), followed by MeOH (4.2 mL). The resulting mixture was allowed to stir for about 75 min, during which time additional sodium borohydride was added. The mixture was poured into $H_2O$ and concentrated under reduced pressure. The residue was partitioned between saturated aqueous NaCl and EtOAc. The organic extract was concentrated in vacuo, and the residue was purified by flash chromatography, eluting with 25% EtOAc/hexanes to afford the title compound (0.80 g, 60%).
4-Fluoro-N-(2-oxo-1-phenyl)ethylbenzamide To a solution of pyridine (1.6 mL, 19.30 mmol) in $CH_2Cl_2$ (18 mL) was added, portionwise, $CrO_3$ (1.16 g, 11.58 mmol). Upon completion of the addition, the mixture was allowed to stir for about 30 min, at which time was added a solution of 4-fluoro-N-(2-hydroxy-1-phenyl)ethylbenzamide (0.50 g, 1.93 mmol) in $CH_2Cl_2$ (35 mL). The resulting mixture was allowed to stir for about 5 min, then was filtered through a pad of florisil and concentrated under reduced pressure to afford the title compound.
1-(4-Pyridyl)-2-(4-fluorophenyl)-4-phenylimidazole To a solution containing 4-fluoro-N-(2-oxo-1-phenyl) ethylbenzamide (0.15 g, 0.58 mmol) and 4-aminopyridine (0.06 g, 0.65 mmol) in toluene (10 mL) was added p-toluenesulfonic acid (0.22 g, 1.20 mmol). The mixture was heated at reflux with azeotropic removal of $H_2O$. After heating at reflux for about 1 h, the mixture was allowed to cool and was partitioned between aqueous $NaHCO_3$ and EtOAc. The organic extract was concentrated under reduced pressure and purified by flash chromatography, eluting with a solvent gradient of 1:5 to 1:1 EtOAc/hexanes. The title compound was obtained (0.04 g, 17%) as a light yellow solid. m.p. 90–92° C.

Example 2

1-(4-Pyridyl)-2-(4-fluorophenyl)-4-(4-hydroxyphenyl)imidazole
Ethyl 4-hydroxyphenylglycine, hydrochloride To a suspension of 4-hydroxyphenylglycine (18.00 g, 0.11 mol) in EtOH (100 mL) was added 20% ethanolic HCl (30 mL). The mixture was heated at reflux for 14 h, then was allowed to cool and was concentrated under reduced pressure. The residue was partitioned between saturated aqueous $NaHCO_3$ and EtOAc, and the organic extract was concentrated in vacuo to afford the title compound (15.00 g, 70%).
N-(4-Fluorobenzoyl)-2-[4-oxy-(4-fluorobenzoyl)phenyl] glycine, ethyl ester To a suspension of ethyl 4-hydroxyphenylglycine, hydrochloride (prepared above) in $CH_3CN$ were added 4-fluorobenzoyl chloride (20 mL, 0.17 mol) and pyridine (15.5 mL, 0.20 mol). The resulting mixture was stirred at room temperature for 5 min, then was partitioned between aqueous $NaHCO_3$ and EtOAc. The organic extract was washed successively with 3 N HCl, saturated aqueous NaCl, 5% aqueous $NaHCO_3$ and saturated aqueous NaCl. The solvent was removed in vacuo to afford the title compound.
4-Fluoro-N-[1-(4-hydroxyphenyl-2-hydroxy)ethyl] benzamide To a solution of N-(4-fluorobenzoyl)-2-[4-oxy-(4-fluorobenzoyl)phenyl]glycine, ethyl ester (1.00 g, 2.27 mmol) in THF (6 mL) was added sodium borohydride (0.22 g, 5.70 mmol). The mixture was warmed to 55° C. and MeOH (1.9 mL) was added over 10 min. Upon completion of the addition, the mixture was poured into $H_2O$ and concentrated under reduced pressure. The residue was partitioned between saturated aqueous NaCl and EtOAc. The organic extract was concentrated in vacuo, and the residue was purified by flash chromatography, eluting with 1:1 EtOAc/hexanes to afford the title compound (0.46 g, 73%).
N-[1-(4-Benzyloxyphenyl-2-hydroxy)ethyl]-4-fluorobenzamide To a solution of 4-fluoro-N-[1-(4-hydroxyphenyl-2-hydroxy)ethyl]benzamide (0.40 g, 1.45 mmol) in acetone were added potassium carbonate (0.30 g, 2.18 mmol) and benzyl bromide (0.29 g, 1.75 mmol). The resulting mixture was heated at reflux for 20 h, then was allowed to cool and was concentrated under reduced pressure. The residue was purified by flash chromatography, eluting with 1:1 EtOAc/hexanes to afford the title compound (0.50 g, 94%).
N-[1-(4-Benzyloxyphenyl-2-oxo)ethyl]-4-fluorobenzamide To a solution of pyridine (1.1 mL, 12.8 mmol) in $CH_2Cl_2$ (10 mL) was added, portionwise, $CrO_3$ (0.78 g, 7.73 mmol). Upon completion of the addition, the mixture was allowed to stir for 30 min, at which time was added a solution of N-[1-(4-benzyloxyphenyl-2-hydroxy)ethyl]-4-fluorobenzamide (0.47 g, 1.28 mmol) in $CH_2Cl_2$ (35 mL). The resulting mixture was allowed to stir for 25 min, then was filtered through a pad of florisil and concentrated under reduced pressure to afford the title compound.
1-(4-Pyridyl)-2-(4-fluorophenyl)-4-(4-benzyloxyphenyl) imidazole To a solution containing N-[1-(4-benzyloxyphenyl-2-oxo) ethyl]-4-fluorobenzamide (0.38 g, 1.00 mmol) and 4-aminopyridine (0.11 g, 1.17 mmol) in toluene was added p-toluenesulfonic acid (0.42 g, 2.20 mmol). The mixture was heated at reflux with azeotropic removal of $H_2O$. After heating at reflux for 1 h, the mixture was allowed to cool and was partitioned between aqueous $NaHCO_3$ and EtOAc. The organic extract was concentrated under reduced pressure and purified by flash chromatography, eluting with a solvent gradient of 1:5 to 1:2 EtOAc/hexanes. The title compound was obtained (0.06 g, 14%) and was crystallized from EtOAc/hexanes.
1-(4-Pyridyl)-2-(4-fluorophenyl)-4-(4-hydroxyphenyl) imidazole A mixture containing 1-(4-pyridyl)-2-(4-fluorophenyl)-4-(4-benzyloxyphenyl)imidazole (0.13 g, 0.3 mmol) and 10% palladium on activated carbon (100 mg) in EtOAc was stirred under an atmosphere of $H_2$ for 10 h, at which time the reaction mixture was filtered through a pad of Celite. The filtrate was concentrated under reduced pressure, and the residue was purified by flash chromatography, eluting with 1:1 EtOAc/hexanes. The material which was isolated was crystallized from EtOAc/hexanes to afford the title compound (0.07 g, 70%). m.p. 230–231° C.

Example 3

1-(4-Pyridyl)-2-(4-fluorophenyl)-4-(4-thiomethylphenyl) imidazole

The compound of Example 3 was produced by the process according to Scheme I; converting 4-thiomethylbenzaldehyde to the amino nitrile and condensing this with 4-fluorobenzoyl chloride. Reduction of the nitrile to the aldehyde was followed by condesation with 4-amino pyridine according to the method of examples 1 and 2 to afford the title compound, m.p. 192–196° C.

Example 4

1-(4-Pyridyl)-2-(4-fluorophenyl)-4-(4-methylsulfinylphenyl)imidazole

Oxidation of 1-(4-pyridyl)-2-(4-fluorophenyl)-4-(4-thiomethylphenyl)imidazole of Example 3 with $K_2S_2O_8$ in acetic acid followed by chromatography on silica and recrystallization afforded the titled sulfoxide, m.p. 201–203° C.

Example 5

1-(4-pyridyl)-2-(4-fluorophenyl)-4-methylimidazole. The compound of Example 5 was produced by the process according to Scheme III, employing methyl aziridine and the imidoyl chloride prepared from the amide formed by condensation of 4-amino pyridine and 4-fluorobenzoyl chloride. Cyclization and dehydrogenation of this adduct affords the title imidazole as a white solid, m/e (rel. int.): 254 [(M+H)$^+$].

Example 6

1-(2-methylpyrid-4-yl)-2-(4-fluororphenyl)-4-(4-thiomethylphenyl)imidazole

This compound was produced by the process according to Scheme I; converting 4-thiomethylbenzaldehyde to the amino nitrile and condensing this with 4-fluorobenzoyl chloride. Reduction of the nitrile to the aldehyde was followed by condensation with 2-methyl-4-amino pyridine according to the method of examples 1 and 2 to afford the title compound, m.p. 144–146° C.

Example 7

1-(2-methylpyrid-4-yl)-2-(4-fluorophenyl)-4-(4-methylsulfinylphenyl)imidazole

Oxidation of 1-(2-methylpyrid-4-yl)-2-(4-fluorophenyl)-4-(4-thiomethylphenyl)imidazole of Example 7 with $K_2S_2O_8$ in acetic acid followed by chromatography on silica and recrystallization afforded the titled sulfoxide, m.p. 160–163° C.

By analogous methods to those described above in Example 1 to 7, and in Schemes I to III herein the following compounds may be produced:

Example 8

1-(4-pyridyl)-2-(4-N,N-dimethylaminomethylphenyl) imidazole

Example 9

1-(4-pyridyl)-2-(4-fluorophenyl)-4-(benzyloxy)imidazole

Example 10

1-(2-methyl-4-pyridyl)-4-(3-chlorophenyl)imidazole

Methods of Treatment

The compounds of Formula (I) can be used in the manufacture of a medicament for the prophylactic or therapeutic treatment of any disease state in a human, or other mammal, which is exacerbated or caused by excessive or unregulated excessive or unregulated cytokine production, more specifically IL-1, IL-$_8$ or TNF production, by such mammal's cell, such as but not limited to monocytes and/or macrophages.

Compounds of Formula (I) are capable of inhibiting proinflammatory cytokines, such as IL-1, IL-$_8$ and TNF and are therefore of use in therapy. IL-1, IL-$_8$ and TNF affect a wide variety of cells and tissues and these cytokines, as well as other luekocyte derived cytokines, are important and critical inflammatory meditators of a wide variety of disease states and conditions. The inhibition of these pro-inflammatory cytokines is of benefit in controlling, reducing and alleviating many of these diseases.

The compounds of Formula (I) are administered in an amount sufficient to inhibit TNF production such that it is regulated down to normal levels, or in some case to subnormal levels, so as to ameliorate or prevent the disease state. Abnormal levels of TNF, for the present invention, constitute levels of 1) free (not cell bound) TNF, greater than or equal to 1 picogram per ml; 2) any cell associated TNF; or 3) the presence of TNF mRNA above basal levels in cells or tissues in which TNF is produced.

The compounds of Formula (I) may be used in the treatment of any disease states mediated by excessive or unregulated TNF production, such as but not limited to rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, pyresis, AIDS and other viral infections, such as cytomegalia virus (CMV), influenza virus, and the herpes family of viruses such as Herpres Zoster or Simplex I and II.

The compounds of Formula (I) may also be used topically as well in the treatment or prophylaxis of inflammatory topical disease states mediated or exacerbated by excessive TNF production respectively, such as for rheumatoid arthritis, rheumatoid spondylitis, osteoarthritis, gouty arthritis and other arthritic conditions, inflamed joints, eczema, psoriasis or other inflammatory skin conditions such as sunburn; inflammatory eye conditions including conjunctivitis; pyresis, pain and other conditions associated with inflammation.

The compounds of Formula (I) may also be used in association with the veterinary field for treatment of TNF mediated diseases such as viral infections. Examples of such viruses include but are not limited to, feline immunodeficiency virus (FIV) or other retroviral infection such as equine infectious anaemia virus, caprine arthritis virus, visna virus, maedi virus and other lentiviruses.

Interleukin-1 (IL-1) has been demonstrated to mediate a variety of biological activities thought to be important in immunoregulation and other physiological conditions such as inflammation [See, e.g., Dinarello et al., *Rev. Infect Disease*, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

The discovery that the compounds of Formulas (I) are inhibitors of cytokines, specifically IL-1 is based upon the effects of the compounds of Formulas (I) on the production of the IL-1 in vitro, on the human monocyte, the assays of which are described herein.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic $\beta$ cells.

Dinarello, J. Clinical Immunology, 5 (5), 287–297 (1985), reviews the biological activities which have been attributed to IL-1. It should be noted that some of these effects have been described by others as indirect effects of IL-1.

The compounds of Formula (I) have also been shown to inhibit the production of Interleukin-8 (NAP-1/IL-8). IL-8 is a chemotactic factor first identified and characterized in 1987. IL-8 is produced by several cell types including mononuclear cells, fibroblasts, endothelial cells, and keratinocytes. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases have the association of increased IL-8 production, which is responsible for the chemotaxis of neutrophils into the inflammatory site. In contrast to other inflammatory cytokines (IL-1, TNF, and IL-6) IL-8 has the unique property of promoting neutrophil chemotaxis. Therefore, the inhibition of IL-8 production would lead to a direct reduction in the neutrophil infiltration.

The discovery of a compound which specifically inhibits IL-1, IL-8, and TNF production will not only contribute to the understanding of how this molecule is synthesized, processed and secreted, but will also provide a therapeutic approach for diseases in which excessive or unregulated IL-1 and TNF production is implicated.

Pharmaceutical Compositions

In order to use a compound of the Formula (I) or a pharmaceutically acceptable salt thereof for the treatment of humans and other mammals it is normally formulated in accordance with standard pharmaceutical practice as a pharmaceutical composition.

This invention, therefore, also relates to a pharmaceutical composition comprising an effective, non-toxic amount of a compound of Formulas (I) and a pharmaceutically acceptable carrier or diluent. The compounds of Formula (I) are administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

The compounds of Formula (I) may be administered topically. Thus, the compounds of Formula (I) may be administered topically in the treatment or prophylaxis of inflammation or other cytokine related diseases in a mammal, such as rheumatoid arthritis, rheumatoid spondylitis, osteoarthritis, gouty arthritis and other arthritic conditions, inflamed joints, eczema, psoriasis or other inflammatory skin conditions such as sunburn; inflammatory eye conditions including conjunctivitis; pyresis, pain and other conditions associated with inflammation.

The amount of a compound of Formula (I), for all methods of use disclosed herein, required for therapeutic effect on topical administration will, of course, vary with the compound chosen, the nature and severity of the inflammatory condition, whether eicosanoid or cytokine mediated, and the animal undergoing treatment, and is ultimately at the discretion of the physician. A suitable, topical, anti-inflammatory dose of an active ingredient, i.e., a compound of Formula (I) is 0.1 mg to 150 mg, administered one to four, preferably two or three times daily.

By topical administration is meant non-systemic administration and includes the application of a compound of Formula (I) externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100 C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as steric or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The methods of the subject invention may be carried out by delivering the monokine activity interfering agent parenterally. The term 'parenteral' as used herein includes intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques.

For all methods of use disclosed herein for the compounds of Formulas (I), the daily oral dosage regimen will preferably be from about 0.05 to about 80 mg/kilogram of total body weight, preferably from about 0.1 to 30 mg/kg, more preferably from about 0.5 mg to 15 mg. The daily parenteral dosage regimen will preferably be from about 0.05 to about 80 mg per kilogram (kg) of total body weight, preferably from about 0.1 to about 30 mg/kg, and more preferably from about 0.5 mg to 15 mg/kg.

The compounds of Formula (I) may also be administered by inhalation. By "inhalation" is meant intranasal and oral inhalation administration. Appropriate dosage forms for such administration, such as an aerosol formulation or a metered dose inhaler, may be prepared by conventional techniques. The preferred daily dosage amount of a compound of Formula (I) administered by inhalation for all methods disclosed herein, is from about 0.01 mg/kg to about 1 mg/kg per day.

It will be recognized by one of skill in the art that the form and character of the pharmaceutically acceptable carrier or diluent is dictated by the amount of active ingredient with which it is to be combined, the route of administration and other well-known variables.

It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques.

It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

EXAMPLES

Without further elaboration, it is believed that one skilled in the art can, using the preceding description, utilize the present invention to its fullest extent. The following Examples are, therefore, to be construed as merely illustrative and not a limitation of the scope of the present invention in any way.

Example A

Inhibitory Effect of compounds of Formula (I) on in vitro IL-1 Production by Human Monocytes The effects of compounds of Formula (I) on the in vitro production of IL-1 by human monocytes was examined using the following protocol.

Bacterial lipopolysaccharide (LPS) was used to induce IL-1 production by human peripheral blood monocytes. IL-1 activity was measured by its ability to stimulate a Interleukin 2 (IL-2) producing cell line (EL-4) to secrete IL-2, in concert with A23187 ionophore, according to the method of Simon et al., *J. Immunol. Methods*, 84, 85, (1985). Human peripheral blood monocytes were isolated and purified from either fresh blood preparations from volunteer donors, or from blood bank buffy coats, according to the procedure of Colotta et al., *J. Immunol.*, 132, 936 (1984). $1 \times 10^6$ of such monocytes were plated in 24-well plates at a concentration of 1–2 million/ml per well. The cells were allowed to adhere for 2 hours, after which time non-adherent cells were removed by gentle washing. Test compounds were then added to the cells for 1 hour (hr) before the addition of lipopolysaccharide (50 ng/ml), and the cultures were incubated at 37° C. for an additional 24 hours. At the end of the incubation period, culture supernatants were removed and clarified of cells and all debris. Culture supernatants were immediately assayed for IL-1 biological activity in the manner described above, as well as for prostaglandin and/or leukotriene concentrations by radioimmunoassay.

The compounds of Formula (I), Examples 1, 2, and 5 are potent inhibitors of in vitro IL-1 production by human monocytes having $IC_{50}$'s between 0.1 μM and 5 μM. The compounds of Examples 3, and 4 exhibited an $IC_{50}$ of >5 μM.

Based on the widely held belief of the role of unmodulated (i.e., excessive) in vivo IL-1 production in causing or aggravating inflammatory responses and other disease states (see, e.g., Fontana et al., supra; Wood et al., supra; Akejima and Dinarello, supra; Habicht and Beck, supra; Chesque et al., supra; Benjamin et al., supra; and Dinarello, supra), and based on the fact that compounds of Formula (I) inhibit in vitro IL-1 production by human macrophages and/or monocytes, the compounds of Formula (I) will inhibit the in vivo IL-1 production by monocytes and/or macrophages in a human in need thereof when used according to the method of the subject invention.

Utility Example B

Inhibitory Effect of compounds of Formula (I) on in vitro TNF production by Human Monocytes Section I: Assay Set-Up The effects of compounds of Formula (I) on the in vitro production of TNF by human monocytes was examined using the following protocol.

Human peripheral blood monocytes were isolated and purified from either blood bank buffy coats or plateletpheresis residues, according to the procedure of Colotta, R. et al., *J. Immunol.*, 132(2):936 (1984). The monocytes were plated at a density of $1 \times 10^6$ cells/ml medium/well in 24-well multi-dishes. The cells were allowed to adhere for 1 hour after which time the supernatant was aspirated and 1 ml fresh medium (RPMI-1640 (Whitaker Biomedical Products, Whitaker, Calif.) containing 1% fetal calf serum and penicillin and streptomycin at 10 units/ml was added. The cells were incubated for 45 minutes in the presence or absence of test compounds at 1 nM–10 uM dose ranges (compounds were solubilized in Dimethyl-sulfoxide/Ethanol such that the final solvent concentration in the culture medium was 0.5% Dimethyl sulfoxide/0.5% Ethanol). Bacterial lipopolysaccharide (*E. coli* 055:B5 [LPS] from Sigma Chemicals Co.) was then added at 100 ng/ml in 10 ml Phosphate Buffered Saline (PBS) and cultures incubated for 16–18 hours at 37° C. in a 5% $CO_2$ incubator. At the end of the incubation period, culture supernatants were removed from the cells, centrifuged at 3000 revolutions per minute (rpm) to remove cell debris and 0.05 ml of the supernatant assayed for TNF activity using the radioimmunoassay described below.

Section II: Radioimmunoassay Procedure for TNF Activity

The assay buffer consisted of 0.01M $NaPO_4$, 0.15M NaCl, 0.025M EDTA and 0.1% sodium azide at pH 7.4. Human recombinant TNF (rhTNF) obtained using the procedure of Chen et al., *Nature*, 330:581–583 (1987) was iodinated by a modified Chloramine-T method described in Section III below. To samples (50 μl culture supernatants) or rhTNF standards, a 1/9000 dilution of polyclonal rabbit anti-rhTNF (Genzyme, Boston, Mass.) and 8000 cpm of $^{125}$I-TNF was added in a final volume of 400 μl buffer and incubated overnight (18 hours) at 4° C. Normal rabbit serum and goat anti-rabbit IgG (Calbiochem) were titrated against each other for maximum precipitation of the anti-rhTNF. The appropriate dilutions of carrier normal rabbit serum (1/200), goat anti-rabbit IgG (1/4) and 25 Units heparin (Calbiochem) were allowed to precipitate and 200 μl of this complex was added per assay tube and incubated overnight at 4° C. Tubes were centrifuged for 30 minutes at 2000 rpm, supernatants were carefully aspirated, and radioactivity associated with the pellets measured in a Beckman Gamma 5500 counter. The logit-log linear transformation curve was used for the calculations. The concentrations of TNF in the samples was read of a standard curve of rhTNF that was linear in the 157 to 20,000 pg/ml range.

Section III: Radioiodination of rhTNF

Iodination of rhTNF was performed using a modified chloramine-T method of Frolik et al., *J. Biol. Chem.*, 259:10995–11000 (1984). Briefly, 5 mg of rhTNF in 5 ml of 20 MM Tris ph 7.5, was diluted with 15 ml of 0.5M $KPO_4$ and 10 ml of carrier free $^{125}$I(100 mCi/ml;ICN). To initiate the reaction, a 5 ml aliquot of a 100 mg/ml (aqueous) chloramine-T solution was added. After 2 minutes at room temperature, an additional 5 ml aliquot was added followed 1.5 minutes later by a final 5 ml addition of chloramine-T. The reaction was stopped 1 minute later by sequential addition of 20 ml of 50 mM Sodium Metabisulfite, 100 ml of 120 mM Potassium Iodide and 200 ml of 1.2 mg/ml Urea. The contents were mixed and the reaction mixture was passed over a pre-packed Sephadex G-25 column (PD 10 Pharmacia), equilibrated and eluted with Phosphate Buffered Saline pH 7.4 containing 0.25% gelatin. The peak radioactivity containing fractions were pooled and stored at −20° C. Specific activity of $^{125}$I-TNF was 80–100 mCi/mg protein. Biological activity of iodinated TNF was measured by the L929 cytotoxicity assay of Neale, M. L. et al., *Eur. J. Can. Clin. Oncol.*, 25(1):133–137 (1989) and was found to be 80% that of unlabeled TNF.

Section IV: Measurement of TNF-ELISA

Levels of TNF were also measured using a modification of the basic sandwich ELISA assay method described in Winston et al., *Current Protocols in Molecular Biology*, Page 11.2.1, Ausubel et al., Ed. (1987) John Wiley and Sons, New York, U.S.A. The ELISA employed a murine monoclonal anti-human TNF antibody, described below, as the capture antibody and a polyclonal rabbit anti-human TNF, described below, as the second antibody. For detection, a peroxidase-conjugated goat anti-rabbit antibody (Boehringer Mannheim, Indianapolis, Ind., U.S.A., Catalog #605222) was added follow d by a substrate for peroxidase (1 mg/ml orthophenylenediamine with 0.1% urea peroxide). TNF levels in samples were calculated from a standard curve generated with recombinant human TNF produced in *E. Coli* (obtained from SmithKline Beecham Pharmaceuticals, King of Prussia, Pa., U.S.A.).

Section V: Production of Anti-Human TNF Antibodies

Monoclonal antibodies to human TNF were prepared from spleens of BALB/c mice immunized with recombinant human TNF using a modification of the method of Kohler and Millstein, *Nature* 256:495 (1975), the entire disclosure of which is hereby incorporated by reference. Polyclonal rabbit anti-human TNF antibodies were prepared by repeated immunization of New Zealand White (NZW) rabbits with recombinant human TNF emulsified in complete Freund's adjuvant (DIFCO, Illinois, U.S.A.).

Results

The compounds of Formula (I), Examples 1 and 2 both demonstrated an IC50's between 0.5 μM and 3.5 μM in the above described assay. The exact mechanism by which any compound of Formula (I) inhibits in vitro TNF production by monocytes is not presently known. This inhibitory activity does not seem to correlate with the property of any of the compounds of Formula (I) in mediating arachidonic acid metabolism inhibition since other nonsteroidal antiinflammatory drugs with potent cyclooxygenase and/or lipoxygenase inhibitory activity do not inhibit TNF production at nontoxic doses. Furthermore, the ability of a compound to inhibit production of prostaglandin and/or leukotriene synthesis does not mean that it will necessarily also inhibit TNF production.

Example C

Inhibitory Effect of compounds of Formula (I) on IL-8 Production

The effects of compounds of Formula (I) on the inhibition of IL-8 production from Human Umbilical Vein Endothelial cells is examined using the following protocol.

Primary human umbilical cord endothelial cells (HUVEC) are obtained from Cell Systems (Kirland, Wash.) and maintained in culture medium supplemented with 15% fetal bovine serum and 1% CS-HBGF consisting of αFGF and heparin. Cells are then diluted 20-fold before being plated (250 μl) into gelating coated 96-well plates. Prior to use, culture medium is replaced with fresh medium (200 μl) 25 μl of either buffer or test compounds at the appropriate concentration is added to each well in quadruplicate wells. This is followed immediately by the addition of 25 μl of the compounds of Formula (I) at concentrations between 1–μM. The plates are allowed to incubate for the appropriate time, as indicated in a humidified incubator at 37° C. with 5% $CO_2$. At the end of the incubation period, supernatant is removed and assayed for IL-8 concentration using an IL-8 ELISA kit obtained from R&D Systems (Minneapolis, Minn.). All data presented is as a mean value (ng/ml) of multiple samples based on the standard curve. IC50's where appropriate are generated by non-linear regression analysis.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of the formula:

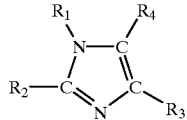

wherein $R_1$ is a mono- or di-substituted 4-pyrimidinyl wherein the substituent is independently selected from the group consisting of hydrogen, $C_{1-4}$ alkyl, halo, O—$C_{1-4}$ alkyl, S—$C_{1-4}$ alkyl, or $N(R_a)_2$;

$R_a$ is hydrogen, $C_{1-6}$alkyl, or $R_a$ may form a heterocyclic ring of 5 to 7 members together with the nitrogen, said ring optionally containing an additional heteroatom selected from the group consisting of oxygen, sulfur or nitrogen;

$R_2$ is mono- or di-substituted phenyl wherein the substituents are independently selected from the group consisting of hydrogen, halo, $S(O)_mR_5$, $OR_6$, halo substituted $C_{1-4}$ alkyl, $C_{1-4}$ alkyl, or $N(R_{12})_2$;

$R_4$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, aryl, or aryl alkyl;

$R_3$ is $(X)_r$—$(Q)_s$—$(Y)_t$;

X is —$(C(R_{10})_2)_n$, —$NR_{13}$, —O— or $S(O)_{m'}$;

r is a number having a value of 0 or 1;

m is a number having a value of 0, 1 or 2;

Q is alkenyl, alkynyl, cycloalkyl, cycloalkenyl, aryl or arylalkyl;

s is a number having a value of 0 or 1;

Y is a substituent selected from the group consisting of hydrogen, $C_{1-10}$ alkyl, halo-substituted $C_{1-10}$ alkyl, halogen, $(C(R_{10})_2)_nOR_8$, $(C(R_{10})_2)_nNO_2$, $(C(R_{10})_2)_nS(O)_{m'}R_{11}$, $C(R_{10})_2)_nSR_8$, $(C(R_{10})_2)_nS(O)_{m}OR_8$, $(C(R_{10})_2)_nS(O)_{m}NR_8R_9$, $X_a$—P(Z)—$(X_aR_{13})_2$, $C(R_{10})_2)_nNR_8R_9$, $(C(R_{10})_2)_nCO_2R_8$, $(C(R_{10})_2)_nOC(O)$—$R_8$, $(C(R_{10})_2)_nCN$, $(C(R_{10})_2)_nCONR_8R_9$, $(C(R_{10})_2)_nC(S)NR_8R_9$, $(C(R_{10})_2)_nNR_{10}C(O)R_8$, $(C(R_{10})_2)_nNR_{10}C(S)R_8$, $(C(R_{10})_2)_nNR_{10}C(Z)NR_8R_9$, $(C(R_{10})_2)_nNR_{10}S(O)_{m}R_{11}$, $(C(R_{10})_2)_nNR_{10}C(=NCN)$—S—$R_{11}$, $(C(R_{10})_2)_nNR_{10}C(=NCN)$—$NR_8R_9$, $(C(R_{10})_2)_nNR_{10}C(O)C(O)$—$NR_8R_9$, $(C(R_{10})_2)_nNR_{10}C(O)C(O)$—$OR_{10}$, $(C(R_{10})_2)_nC(=NR_{10})$—$NR_8R_9$, $(C(R_{10})_2)_nC(=NR_{10})$—$ZR_{11}$, $(C(R_{10})_2)_n$—OC(Z)—$NR_8R_9$, $(C(R_{10})_2)_nNR_{10}S(O)_{m}CF_3$, or $(C(R_{10})_2)_nNR_{10}C(O)OR_{10}$;

t is a number having a value of 0, 1, 2, or 3;

Xa is independently —$(C(R_{10})_2)_n$, —$NR_8$—, —O— or —S—;

Z is oxygen or sulfur;

m' is a number having a value of 1 or 2;

n is a number having a value of 0 to 10;

$R_5$ is hydrogen, $C_{1-4}$ alkyl, $C_{2-4}$ alkenyl, $C_{2-4}$ alkynyl, $C_{3-7}$ cycloalkyl, $C_{5-7}$ cycloalkenyl, aryl, or $N(R_7)_2$; provided that when m is 1 or 2 then $R_5$ is not hydrogen;

$R_6$ is hydrogen, $C_{1-4}$ alkyl, halo substituted $C_{1-4}$ alkyl, $C_{2-4}$ alkenyl, $C_{2-4}$ alkynyl, $C_{3-7}$ cycloalkyl, $C_{5-7}$ cycloalkenyl, or aryl;

$R_7$ is hydrogen, $C_{1-4}$ alkyl, $C_{2-4}$ alkenyl, $C_{2-4}$ alkynyl, aryl, or may form a heterocyclic ring of 5 to 7 members together with the nitrogen, said ring optionally containing an additional heteroatom selected from the group consisting of oxygen, sulfur or nitrogen; provided that when $R_5$ is $N(R_7)_2$ then m is 1 or 2;

$R_8$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, aryl, or aryl alkyl;

$R_9$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, aryl, or aryl alkyl or $R_8$ and $R_9$ may together form a heterocyclic ring of 5 to 7 members together with the nitrogen, said ring optionally containing an additional heteroatom selected from the group consisting of oxygen, sulfur or nitrogen;

$R_{10}$ is hydrogen, or $C_{1-4}$ alkyl;

$R_{11}$ is $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl;

$R_{12}$ is hydrogen, $C_{1-4}$ alkyl, aryl, or may form a heterocyclic ring of 5 to 7 members together with the nitrogen;

$R_{13}$ is hydrogen, $C_{1-10}$ alkyl, cycloalkyl, aryl, or aryl alkyl;

or a pharmaceutically acceptable salt thereof.

2. The compound according to claim 1 wherein s is 0.

3. The compound according to claim 2 wherein r is 0.

4. The compound according to claim 3 wherein Y is alkyl, $(C(R_{10})_2)_nOR_8$, $(C(R_{10})_2)_nS(O)_{m'}R_{11}$, $C(R_{10})_2)_nSR_8$, $(C(R_{10})_2)_nS(O)_{m'}OR_8$, $(C(R_{10})_2)_nS(O)_{m'}NR_8R_9$, $X_aP(Z)(X_aR_{13})_2$, $C(R_{10})_2)_nNR_8R_9$, $(C(R_{10})_2)_nC(O)OR_8$, $(C(R_{10})_2)_nOC(O)R_8$, $(C(R_{10})_2)_nC(O)NR_8R_9$, $(C(R_{10})_2)_nNR_{10}C(=NCN)$—$NR_8R_9$, or $(C(R_{10})_2)_nNR_{10}S(O)_mR_{11}$.

5. The compound according to claim 4 wherein Y is alkyl, $(C(R_{10})_2)_nOR_8$, $(CH_2)_nS(O)_{m'}R_{11}$, $(CH_2)_nCO_2R_8$, $(C(R_{10})_2)_nNR_{10}C(=NCN)NR_8R_9$, $(C(R_{10})_2)_nNR_8R_9$, or $X_aP(Z)(X_aR_{13})$; and n is 0 to 4.

6. The compound according to claim 1 wherein s is 1.

7. The compound according to claim 6 wherein Q is aryl.

8. The compound according to claim 7 wherein Y is alkyl, $(C(R_{10})_2)_nOR_8$, $C(R_{10})_2)_nS(O)_{m'}R_{11}$, $(C(R_{10})_2)_nSR_8$, $(C(R_{10})_2)_nS(O)_{m'}OR_8$, $(C(R_{10})_2)_{n\ S(O)_{m'}}NR_8R_9$, $X_aP(Z)(X_aR_{13})_2$, $(C(R_{10})_2)_nNR_8R_9$, $(C(R_{10})_2)_nC(O)OR_8$, $(C(R_{10})_2)_nOC(O)R_8$, $(C(R_{10})_2)_nC(O)NR_8R_9$, $(C(R_{10})_2)_nNR_{10}C(=NCN)NR_8R_9$, or $(C(R_{10})_2)_nNR_{10}S(O)_mR_{11}$.

9. The compound according to claim 7 wherein r is 0, or r is 1 and X is —$(C(R_{10})_2)_n$.

10. The compound according to claim 7 wherein $R_4$ is hydrogen or alkyl.

11. The compound according to claim 1 wherein $R_2$ is a mono-substituted phenyl and wherein the substituent is selected from the group consisting of hydrogen, halo, $S(O)_mR_5$, $OR_6$ or $C_{1-4}$ alkyl.

12. The compound according to claim 1 wherein $R_2$ is a mono-substituted phenyl and wherein the substituent is selected from the group consisting of hydrogen, halo, $S(O)_mR_5$, $OR_6$, or $C_{1-4}$ alkyl; r is 0, s is 1, Q is aryl, Y is hydrogen, alkyl, —$(C(R_{10})_2)_nOR_8$, —$(C(R_{10})_2)_nS(O)_{m'}R_{11}$, —$(C(R_{10})_2)_nSR_8$, —$(C(R_{10})_2)_nS(O)_{m'}OR_8$, —$(C(R_{10})_2)_nS(O)_{m'}NR_8R_9$, —$X_a$—P(Z)—$(X_aR_{13})_2$, —$(C(R_{10})_2)_nNR_8R_9$, —$(C(R_{10})_2)_nCO_2R_8$, —$(C(R_{10})_2)_nOC(O)$—$R_8$, —$(C(R_{10})_2)_nCONR_8R_9$, —$(C(R_{10})_2)_nNR_{10}C(=NCN)$—$NR_8R_9$, or —$(C(R_{10})_2)_nNR_{10}S(O)_mR_{11}$, $R_4$ is hydrogen or methyl, $R_8$ is hydrogen, $C_{1-4}$ alkyl, or may optionally cyclize with $R_9$ to form a 5 membered heterocyclic ring together with the nitrogen to which they are attached.

13. A pharmaceutical or veterinary composition comprising an effective amount of a compound according to claim 1 and a pharmaceutically or veterinary acceptable carrier or diluent.

14. A method for treating a cytokine mediated disease selected from arthritis, osteoarthritis, rheumatoid arthritis or gout in a mammal in need of such treatment, which comprises administering to said mammal an effective cytokine interfering amount of a compound of formula (I), according to claim 1.

15. The method according to claim 14 wherein the cytokine inhibited is IL-1.

16. The method according to claim 14 wherein the cytokine inhibited is TNF.

17. The method according to claim 14 wherein the cytokine inhibited is IL-8.

* * * * *